United States Patent [19]
McGall et al.

[11] Patent Number: 5,412,087
[45] Date of Patent: May 2, 1995

[54] SPATIALLY-ADDRESSABLE IMMOBILIZATION OF OLIGONUCLEOTIDES AND OTHER BIOLOGICAL POLYMERS ON SURFACES

[75] Inventors: Glenn H. McGall, Mountain View; Stephen P. A. Fodor, Palo Alto; Edward L. Sheldon, Menlo Park, all of Calif.

[73] Assignee: Affymax Technologies N.V., Curaco, Netherlands Antilles

[21] Appl. No.: 874,849

[22] Filed: Apr. 24, 1992

[51] Int. Cl.$^6$ .................. C07H 17/00; C12N 11/06
[52] U.S. Cl. .................. 536/24.3; 536/22.1; 435/181; 436/532; 530/816
[58] Field of Search ............ 436/527, 528, 578, 507, 436/807, 961, 962, 973; 435/187; 536/27, 24.3, 22.1

[56] References Cited

U.S. PATENT DOCUMENTS

| | | | |
|---|---|---|---|
| 4,282,287 | 8/1981 | Giese | 428/407 |
| 4,542,102 | 9/1985 | Dattagupta et al. | 435/6 |
| 4,562,157 | 12/1985 | Lowe et al. | 435/291 |
| 4,681,870 | 7/1987 | Balint, Jr. et al. | 502/403 |
| 4,762,881 | 8/1988 | Kauer | 525/54.11 |
| 4,937,188 | 6/1990 | Giese et al. | 435/41 |
| 5,011,770 | 4/1991 | Kung et al. | 435/6 |
| 5,077,085 | 12/1991 | Schnur et al. | 427/98 |
| 5,077,210 | 12/1991 | Eigler et al. | 435/176 |
| 5,079,600 | 1/1992 | Schnur et al. | 357/4 |
| 5,143,854 | 9/1992 | Pirrung et al. | 436/516 |
| 5,288,514 | 2/1994 | Ellman | 427/2 |
| 5,324,633 | 7/1994 | Fodor et al. | 435/6 |

FOREIGN PATENT DOCUMENTS

| | | |
|---|---|---|
| 2233654 | 1/1991 | United Kingdom . |
| 8911548 | 11/1989 | WIPO . |
| 9007582 | 7/1990 | WIPO . |
| 9015070 | 12/1990 | WIPO . |
| 9100868 | 1/1991 | WIPO . |
| 9107087 | 5/1991 | WIPO . |
| 9110746 | 7/1991 | WIPO . |

OTHER PUBLICATIONS

Bhatia et al., Immobilization of actylcholinesterase on solid surfaces: chemistry and activity studies, Sensors and Actuators B,3 (1991)311–317.
Bhatia et al., New Approach to Producing Patterened Biomolecular Assemblies, J. Am. Chem. Soc 1992, 114, 4432–4433.
McCray, J. et al., Properties and Uses of Photoreactive Caged Compounds, Annu. Rev. Biophys, Biophys. Chem., 1989, 239–70.
Dower et al., Chapter 28. The search for molecular Diversity (II): Recombinant and Synthetic Randomized Peptide Libraries, Molecular Diversity/Peptide Libraries, 271–280.
Fodor et al., Light-Directed, Spatially Addressable Parrallel Chemical Synthesis, Science vol. 285, Feb. 15, 1991, 767–773.
CA 116 (11): 106500s; Stjernloef (1991).

*Primary Examiner*—Douglas W. Robinson
*Assistant Examiner*—Anita Varma
*Attorney, Agent, or Firm*—Lauren L. Stevens

[57] ABSTRACT

Substrates with surfaces comprising compounds with thiol functional groups protected with a photoremovable protecting group can be used to construct arrays of immobilized anti-ligands, such as oligonucleotide probes or other biological polymers. The arrays can be used in assays to detect the presence of complementary nucleic acids in a sample. Spatially addressed irradiation of predefined regions on the surface permits immobilization of oligonucleotides and other biological polymers at the activated regions on the surface. Cycles of irradiation on different regions of the surface and immobilization of different anti-ligands allow formation of an immobilized matrix of anti-ligands at defined sites on the surface. The immobilized matrix of anti-ligands permits simultaneous screenings of a liquid sample for ligands having high affinities for certain anti-ligands of the matrix.

7 Claims, 1 Drawing Sheet

SPATIALLY-ADDRESSABLE IMMOBILIZATION OF OLIGONUCLEOTIDES AND OTHER BIOLOGICAL POLYMERS ON SURFACES

BACKGROUND OF THE INVENTION

1. Field of the Invention

The present invention relates generally to methods and compositions useful for immobilizing oligonucleotides and other biological polymers on surfaces. The immobilized biological polymers, which can be, for example, oligonucleotides or polypeptides, are useful in a variety of screening and assay methodologies. The present invention has applications in the fields of molecular biology, biochemistry, pharmacology, and medical diagnostic technology.

2. Description of Related Art

Many different methods are known for attaching biological molecules to solid supports. See generally, *Affinity Techniques, Enzyme Purification: Part B, Meth. Enz.* 34 (ed. W. B. Jakoby and M. Wilchek, Acad. Press, N.Y. 1974) and *Immobilized Biochemicals and Affinity Chromatography, Adv. Exp. Med. Biol.* 42 (ed. R. Dunlap, Plenum Press, N.Y. 1974), incorporated herein by reference. The patent literature also describes a number of different methods for attaching biological molecules to solid supports. For example, U.S. Pat. No. 4,282,287 describes a method for modifying a polymer surface through the successive application of multiple layers of biotin, avidin, and extenders. U.S. Pat. No. 4,562,157 describes a technique for attaching biochemical ligands to surfaces by attachment to a photochemically reactive arylazide. Irradiation of the azide creates a reactive nitrene that reacts irreversibly with macromolecules in solution resulting in the formation of a covalent bond. The high reactivity of the nitrene intermediate, however, results in both low coupling efficiencies and many potentially unwanted products due to nonspecific reactions.

U.S. Pat. No. 4,681,870 describes a method for introducing free amino or carboxyl groups onto a silica matrix; the groups may subsequently be covalently linked to a protein in the presence of a carbodiimide. Also, U.S. Pat. No. 4,762,881 describes a method for attaching a polypeptide chain to a solid substrate by incorporating a light-sensitive unnatural amino acid group into the polypeptide chain and exposing the product to low-energy ultraviolet light.

A variety of techniques have also been developed for attaching oligonucleotides to surfaces. For example, U.S. Pat. No. 4,542,102 describes a method employing a photochemically active reagent (e.g., a psoralen compound) and a coupling agent, which attaches the photoreagent to the substrate. Photoactivation of the photoreagent binds a nucleic acid sequence to the substrate to give a surface-bound probe for a complementary oligonucleotide. However, this method has low quantum yields in protic solvents, lacks spatial directability, and relies upon initial affinity between the photoreagent and nucleic acids to bind the nucleic acids to the surface prior to photoactivation.

U.S. Pat. No. 4,937,188 describes methods for forming maleimide-thiol linkages between a solid support and a molecular tether. In one example, thiol groups on sepharose are reacted with maleimide groups on an RNA polymer, which serves as the tether, and the RNA polymer is reacted with a protein, also via a maleimide-thiol linkage. In another example, maleimide groups immobilized on a solid support are reacted with sulfhydryl RNAse forming RNAse-agarose. U.S. Pat. No. 5,011,770 describes the use of a maleimide-thiol linkage to bind an enzyme label to a binding protein, which in turn binds to single stranded DNA. The patent describes that the binding protein can also be attached to a solid support. The maleimide-thiol linkage is thus spatially separated from the actual linkage between the peptide and the solid support.

PCT patent publication No. 90/07582 describes polyacrylamide supports on which are immobilized oligonucleotides. The oligonucleotides are derivatized at the 5'-terminus with thiol groups that are reacted with bromoacetyl groups on the polyacrylamide support during the immobilization process. PCT patent publication No. 91/00868 discloses solid supports on which oligonucleotides are immobilized via a 5'-dithio linkage.

The immobilization of biological polymers on solid supports has also had significant impact on drug discovery and medical diagnostic methods. One important invention in these fields is described in U.S. Pat. No. 5,143,854 an in Ser. Nos. 624,120, filed Dec. 6, 1990, and 805,727, filed Dec. 6, 1991, and in PCT patent publication No. 90/15070 to Pirrung et al., each of which is incorporated herein by reference. In brief, the invention provides methods and reagents for synthesizing very large numbers of different compounds, particularly biological polymers, in distinct and spatially-addressable locations in a very small area on a substrate. Another description of the invention is found in Fodor et al., 15 Feb. 1991, *Science* 251:767-773, and the integration of the invention with other drug discovery methods is described in Dower and Fodor, 1991, *Ann. Rep. Med. Chem.* 26:271-280. A related method uses a photoactivateable derivative of biotin as the agent for immobilizing a biological polymer of interest onto a solid support; see U.S. Pat. No. 5,252,743, and PCT patent publication No. 91/07087 to Barrett et al., each of which is incorporated herein by reference.

Recent approaches to genetic analysis are increasingly placing importance on performing parallel hybridizations in an array format. Applications of the parallel hybridization format include generating diagnostic arrays for tissue typing or diagnosis of genetic disorders (see PCT patent publication No. 89/11548, incorporated herein by reference), DNA sequencing by hybridization, DNA fingerprinting, and genetic mapping (see U.S. patent application Ser. Nos. 624,114, now abandoned and 626,730, filed Dec. 6, 1990, each of which is incorporated herein by reference; see also Khrapko et al., 1991, *J. DNA, Seq. Map.* 375-388). In these applications of probe arrays, the information content of the array increases as the number of probes is increased. The size limit of the array is dictated by the ability to automate and miniaturize the fabrication of the array.

Thus, there exists a need for improved methods for attaching a broad range of anti-ligands to predefined regions of a solid support surface. The methods should efficiently provide stable attachment of selected polymers to the activated surface regions, yet attachment should be restricted to the activated regions. The present invention fulfills these and other needs.

SUMMARY OF THE INVENTION

Novel methods and compositions of matter are provided for immobilizing oligonucleotides and other biological polymers on predefined regions of a surface of a solid support. The methods involve attaching to the surface a thiol functional group protected with a photochemical protecting group so that the thiol has very low reactivity for other functional groups reactive with thiols. The protected thiol is convertible by irradiation to a fully reactive thiol capable of immobilizing a desired biological polymer such as a nucleic acid, protein, or polysaccharide. Predefined regions of the surface are selectively irradiated to convert the protected thiols in the predefined regions to reactive thiol groups. The desired biological polymers subsequently can be immobilized on the activated regions of the surface.

The spatial addressability afforded by the method of the present invention allows the formation of patterned surfaces having preselected reactivities. For example, by using lithographic techniques known in the semiconductor industry, light can be directed to relatively small and precisely known locations on the surface. Thus, the present invention can be used to activate discrete, predetermined locations on the surface for attachment of biological polymers. The resulting surface will have a variety of uses. For example, direct binding assays can be performed in which nucleic acids in a sample can be simultaneously tested for affinity to a number of different oligonucleotide probes attached to the surface. Binding can be detected by a technique such as autoradiography when one of the binding moieties is radioactively labelled. Alternatively, fluorescence and optical measuring techniques can be used to detect the binding. By determining the locations and amount of label on the surface, one can simultaneously screen ligands for affinity to a plurality of anti-ligands.

Thus, the present invention provides methods for building arrays of biomolecules using photolithographic techniques. The method obviates the need to separate reactants spatially, because the substrate is unreactive until specific sites are activated with light. In one embodiment, the method involves the light-directed immobilization of oligonucleotides on a glass surface derivatized with a caged thiol reagent. The method can be used to fabricate large arrays of oligonucleotide probes.

A further understanding of the nature and advantages of the invention may be realized by reference to the remaining portions of the specification.

DETAILED DESCRIPTION OF THE PREFERRED EMBODIMENTS

The following terms have the following meanings and abbreviations as used herein:

"Surface" is any generally two-dimensional structure on a solid substrate and may have steps, ridges, kinks, terraces, and the like without ceasing to be a surface.

"Predefined Region" is a localized area on a surface which is or is intended to be activated. The predefined region may have any convenient shape, e.g., circular, rectangular, elliptical, etc.

"Crosslinking Group" is a bifunctional chemical entity that serves to connect a binding member to a surface. Usually, crosslinking groups are heterobifunctional and so have different chemical reactivities on either end of the linking group.

"Biological Polymer" is a compound composed of monomeric units linked to one another that has biological activity or is reactive with a compound that has biological activity. Nucleic acids such as RNA and DNA are biological polymers, and peptides, proteins, and carbohydrates are also biological polymers. Synthetic, non-naturally occurring monomers can be used to construct a biological polymer. For instance, carbamates, phosphonates, sulfonamides, and sulfoxides are examples of monomers that can be used to construct biological polymers.

"Anti-ligand" is a molecule that has an affinity for a given ligand and can be immobilized on a predefined region of a surface. Anti-ligands may be naturally-occurring or synthetic molecules. Anti-ligands can be employed in an unaltered state or as aggregates with other species. Anti-ligands can be reversibly attached, covalently or noncovalently, to a binding member, either directly or via a specific binding substance. "Reversibly attached" means that the binding of the anti-ligand (or specific binding member or ligand) is reversible and has, therefore, a substantially nonzero reverse, or unbinding, rate. Such reversible attachments can arise from noncovalent interactions, such as electrostatic forces, van der Waals forces, hydrophobic (i.e., entropic) forces, and the like. Furthermore, reversible attachments also may arise from certain, but not all covalent bonding reactions. Examples include, but are not limited to, attachment by the formation of hemiacetals, hemiketals, imines, acetals, ketals, and the like (See, Morrison et al, "Organic Chemistry" 2nd, ed., Ch. 19 (1966), which is incorporated herein by reference). Examples of anti-ligands that can be employed in the practice of the present invention include, but are not restricted to, cell membrane receptors, monoclonal antibodies and antisera reactive with specific antigenic determinants (such as on viruses, cells, or other materials), hormones, drugs, oligonucleotides, peptides, enzymes, substrates, cofactors, lectins, sugars, oligosaccharides, cells, cellular membranes, and organelles.

"Ligand" is a solvated molecule that is recognized by a particular anti-ligand. Examples of ligands that can be investigated with the present invention include, but are not restricted to, agonists and antagonists for cell membrane receptors, toxins and venoms, viral epitopes, hormones, opiates, steroids, hormone receptors, peptides, enzymes, enzyme substrates, cofactors, drugs, lectins, sugars, oligonucleotides, oligosaccharides, proteins, and monoclonal antibodies.

The present invention provides methods for forming predefined regions on a surface of a solid support, wherein the predefined regions comprise caged thiol groups that can be activated and then used to immobilize ligands and/or anti-ligands. The caged thiols attached to the surface can be selectively activated in predefined regions. The activated thiols are then used to immobilize compounds, e.g. anti-ligands, on the predefined regions of the surface. The above procedure can be repeated at the same or different sites on the surface so as to provide a surface with a plurality of regions containing the same or different anti-ligands. When the anti-ligands have a particular affinity for one or more ligands, screenings and assays for the ligands can be conducted in the regions of the surface containing the anti-ligands.

The present method employs novel caged thiols attached to the substrate. Caged (unactivated) thiols have relatively low reactivity with functional groups typically reactive with thiols when compared with uncaged thiols. Thus, the caged thiols are protected until a suitable source of energy is applied to the regions of the surface to be activated. Upon application of a suitable energy source, the caging groups labilize, thereby presenting the thiol. Typically, the energy source will be light. Once the thiols on the surface are activated, the thiols can be attached to and reacted with a biological polymer of interest, typically a nucleic acid or other anti-ligand.

Prior to activation, however, the thiol groups on the surface are "caged" with a protecting group. The protecting groups can either be attached to the compounds carrying the thiol functional group after those compounds have been attached to the surface or, more preferably, the protecting groups will be attached to the compounds carrying the thiol functional group prior to attaching the thiol functional group to the surface. Surface attachment of compounds carrying a thiol group or protected thiol group can be effected through the use of crosslinking groups. The crosslinking groups will usually, though not always, be heterobifunctional chemical species having a first reactivity that permits the crosslinking group to bind readily to the surface and a second reactivity that permits the crosslinking group to bind readily with compounds carrying a thiol group or protected thiol group.

As noted above, predefined regions on the surface can be activated for ultimate immobilization of anti-ligands in the predefined regions by selectively irradiating predefined regions to convert photoactivatable thiol groups in the predefined region to fully reactive thiol groups. The free protecting group may or may not undergo decomposition reactions. The byproducts of irradiation of the protecting group will usually be washed from the surface if the byproducts interfere with subsequent reactions.

An immobilized anti-ligand on a surface will have a specific binding affinity for a particular ligand. If a surface comprising immobilized anti-ligands is exposed to a labeled ligand under conditions conducive to ligand binding to anti-ligand, then the resulting surface can be washed free of unbound ligand and analyzed for the presence of labeled ligand. The labels will provide markers localized at the predefined regions on the surface corresponding to the presence of anti-ligands for the ligand at those predefined regions. The presence of target ligand can be determined by analyzing appropriately for the loss or buildup of label on the predefined regions of the surface.

To prepare the surface comprising immobilized biological polymers of the invention, one first selects a substrate for surface modification. Virtually any solid substrate can be employed in the method of the invention. The substrate can be biological, nonbiological, organic, inorganic, or a combination of any of these materials, existing as particles, strands, precipitates, gels, sheets, tubing, spheres, containers, capillaries, pads, slices, films, plates, slides, etc. The substrate can have any convenient shape, such as a disc, square, sphere, circle, etc. The substrate and the surface of the substrate preferably form a rigid support on which to carry out the reactions described herein.

The substrate and the surface should also be chosen to provide appropriate light-absorbing characteristics. For instance, the substrate can be a polymerized Langmuir Blodgett film, functionalized glass, Si, Ge, GaAs, GaP, $SiO_2$, $SIN_4$, modified silicon, or any one of a wide variety of polymers such as (poly)tetrafluoroethylene, (poly)vinylidenedifluoride, or combinations thereof. Other substrate materials will be readily apparent to those of skill in the art upon review of this disclosure. In a preferred embodiment the substrate is flat glass or single-crystal silicon with surface features of less than 10 angstroms.

Surfaces on the solid substrate will usually, though not always, be composed of the same material as the substrate. Thus, the surface may be composed of any of a wide variety of materials, for example, polymers, plastics, resins, polysaccharides, silica or silica-based materials, carbon, metals, inorganic glasses, membranes, etc., provided only that caged thiols can be attached to the surface of the substrate. Preferably, the surface will contain reactive groups, which could be carboxyl, amino, hydroxyl, or the like. Most preferably, the surface will be optically transparent and will have surface Si—OH functionalities, such as are found on silica surfaces.

The surface of the substrate is preferably provided with a layer of crosslinking groups, although one of ordinary skill will understand that the crosslinking groups are not required elements of the invention. The crosslinking groups are preferably of sufficient length to permit thiol groups on the surface, as well as biological polymers covalently attached to the thiol groups, to interact freely with compounds in solution. Crosslinking groups can be selected from any suitable class of compounds, for example, aryl acetylenes, ethylene glycol oligomers containing two to ten monomer units, diamines, diacids, amino acids, or combinations thereof. Other crosslinking groups may be used in view of this disclosure.

Crosslinking groups can be attached to the surface by a variety of methods that are readily apparent to one having skill in the art. For example, crosslinking groups may be attached to the surface by siloxane bonds formed via reactions of crosslinking groups bearing trichlorosilyl or trisalkoxy groups with hydroxyl groups on the surface of the substrate. Preferably, the crosslinking group used with a glass surface is t-BOC-aminopropyltriethoxysilane. The crosslinking groups can optionally be attached in an ordered array, i.e., as parts of the head groups in a polymerized Langmuir Blodgett film. Clearly, the type of crosslinking group selected, and the method selected for attaching the crosslinking group to the surface, will depend primarily on the crosslinking group having suitable reactivity with the compound carrying the thiol group desired to be attached to the surface.

Additional length may be added to the crosslinking groups by the addition of single or multiple linking groups. Such linking groups are preferably heterobifunctional, having one end adapted to react with the crosslinking groups and the other end adapted to react with the compound carrying the thiol group or another linking group. The linking groups may be attached by a variety of methods that are readily apparent to one skilled in the art, for instance, by esterification or amidation reactions of an activated ester of the linking group with a reactive hydroxyl or amine on the free end of the crosslinking group. A preferred linking group is N-BOC-6-aminocaproic acid (or N-BOC-6-aminohexanoic acid) attached by the BOP-activated ester. After deprotection to liberate the free amine terminus, another N-BOC-aminocaproic linker can be added. Attachment of crosslinking and linking groups to caged thiol compounds are discussed more fully below.

Many methods are available for immobilizing the compound carrying the thiol group of the present invention on surfaces. The compound carrying the thiol group can be linked to the surface and later provided with protecting (caging) groups. More preferably,.compounds carrying the thiol group will be attached to the surface in a protected form. The method chosen for linking the compound carrying the thiol group to the surface will depend upon the chemical properties of the compound carrying the thiol group selected for attachment to the surface. A preferred method for immobilizing the compound carrying the thiol group of the present invention involves chemical derivatization or activation of the caged compound carrying the thiol group prior to attachment to the surface or linker.

This derivative or activated species is then reacted with functionalities on the substrate to give the desired linkage. For example, one method for attaching a compound carrying the thiol group to a surface employs a bifunctional crosslinking reagent, such as diepoxide, which both activates the surface and provides a group that reacts with an activated compound carrying the thiol group. Alternatively, some surfaces can be activated with cyanogen bromide. Likewise, in the presence of a carbodiimide or other activating agent, for example, an amine group on the surface can be coupled to a carboxyl group of a compound carrying the thiol group to effect the immobilization.

In one embodiment, the compound carrying the thiol group is a caged cysteine, or other thiol-containing synthetic amino acid. Such compounds are useful in a wide variety of applications; for instance, one could carry out amino acid addition on either the amino or carboxyl groups of the protected cysteine and then, after photoactivation, derivatize the side chain of the cysteine residue. Such techniques will often employ different classes of protecting groups, so that one can modify the immobilized molecules at different reactive groups. These techniques include cyclization, where the cyclization step is controlled by the use of protecting groups on the two amino acid residues undergoing cyclization that are different from the protecting groups on amino acid residues that are not to be cyclized. See U.S. patent application Ser. No. 796,727, filed Nov. 22, 1991, incorporated herein by reference.

Many different protecting (caging) groups can be employed for modifying thiol groups to give the caged thiols of the present invention. The protecting groups should be sterically large enough to reduce the reactivity of the caged thiol with other substances to permit operability of the invention, although protecting groups utilizing other types of interactions, such as electronic, hydrophobic, etc., could be used. The selection of suitable caging groups will depend upon the size and chemical nature of the compound carrying the thiol group chosen and will be readily apparent to one skilled in the art.

The caging groups are photoactivatable. The properties and uses of photoreactive caged compounds have been reviewed. See McCray et al, 1989, Ann. Rev. Biophys. Biophys. Chem. 18:239–270, which is incorporated herein by reference. Preferably, the photosensitive cages will be activatable by low energy ultraviolet or visible light. Many, although not all, of the photosensitive protecting groups are aromatic compounds. Suitable photoremovable protecting groups are also described in, for example, Patchornik, 1970, J. Am. Chem. Soc. 92:6333, and Amit et al, 1974, J. Org. Chem. 39:192, which are incorporated herein by reference. See also, Calbiochem Catalog (San Diego, Calif., 1989), pp. 244–247, incorporated herein by reference. More preferably, the photosensitive protecting group will be a nitro benzylic compound, such as o-nitrobenzyl or benzylsulfonyl groups. In a preferred embodiment, 6-nitroveratryloxycarbonyl (NVOC); 6-nitropiperonyloxycarbonyl (NPOC); alpha, alpha-dimethyldimethoxybenzyloxycarbonyl (DDZ), methyl 6-nitroveratryloxycarbonyl (MenVOC), methyl-6-nitropiperonyloxycarbonyl (MeNPOC), or 1-pyrenylmethyl is employed.

Clearly, many photosensitive protecting groups are suitable for use in the present method. Some examples of acceptable photosensitive protecting groups are presented in Table 1, below, together with their corresponding wavelengths for deprotection.

TABLE 1

| Protecting Groups | |
|---|---|
| Group | Deprotection Wavelength |
| 6-nitroveratryloxycarbonyl (NVOC) | UV (300–350 nm) |
| dimethyldimethoxybenzyloxycarbonyl (DDZ) | UV (280–300 nm) |
| nitrobenzyloxycarbonyl (NBOC) | UV (300–350 nm) |
| 5-bromo-7-nitroindolinyl (BNI) | UV (420 nm) |
| O-hydroxy-alpha-methyl-cinnamoyl (HMC) | UV (300–350 nm) |
| 2-oxymethylene anthraquinone (OMA) | UV (350 nm) |

Once the surface is covered with a plurality of caged thiol groups, selected regions of the surface may be irradiated to provide free thiols on the surface. In a preferred embodiment, the radiation is UV, near IR, or visible light. The light source may be coherent or non-coherent. In some embodiments, the exposed area is less than about 1 cm2 or less than about 1 mm2. In preferred embodiments the irradiated area will be composed of a pattern of smaller, discrete irradiated areas, each of which is less than about 10,000 $\mu m^2$ or, more preferably, less than about 100 $\mu m^2$. Preferably, each individual synthesis site in the pattern is about 50 to 500 $\mu M^2$. Spaces between activated regions are not critical and will generally be greater than about 1 $\mu m$. Exposure of the surface to light will typically be carried out with a suitable mask using photolithographic techniques well known in the semiconductor industry and described in, for example, Sze, VLSI Technology, McGraw-Hill (1983), which is incorporated herein by reference.

In one embodiment, the mask is a transparent support material coated with a layer of opaque material. Portions of the opaque material are removed, leaving opaque material in the precise pattern desired on the substrate surface. The mask is brought into close proximity with or directly into contact with the surface. Openings in the mask correspond to locations on the surface where one desires to photoremove protecting groups from thiol groups. Alignment may be performed using conventional alignment techniques in which alignment marks are used to overlay accurately successive masks with previous patterning steps. Other alignment techniques may be used, for example, interferometric techniques such as the one described in Flanders et al, 1977, *App. Phys. Lett.* 31:426–428, which is incorporated herein by reference.

To enhance contrast of light applied to the substrate, one may place contrast enhancement materials between the mask and the substrate. This contrast enhancement layer may comprise a molecule, such as quinone diazide, which is decomposed by light. The light may be from a conventional incandescent source, an arc lamp, a laser, or the like. If noncoherent sources of light are used, one may utilize a thick or multi-layered mask to prevent spreading of the light on the substrate. Generally, lasers may be preferable, because lasers can more easily provide wavelengths particularly suited for a chromophore of the photosensitive group.

While the invention is illustrated primarily herein by way of the use of a mask to illuminate the substrate, other techniques may also be used. For example, the substrate may be rotated or oriented under a modulated laser or diode light source. Such techniques are discussed in, for example, U.S. Pat. No. 4,719,615, which is incorporated herein by reference. The substrate may be irradiated either in contact with or not in contact with a solution but usually is irradiated in contact with a solution.

The solution may contain reagents to prevent byproducts of irradiation from interfering with subsequent binding reactions. Such byproducts might include, for example, carbon dioxide, nitrosocarbonyl compounds, styrene derivatives, indole derivatives, and products of the photochemical reactions of such compounds. Reagents added to the solution may include, for example, acidic or basic buffers, thiols, substituted hydrazines and hydroxylamines, reducing agents (e.g., NADH or bisulfite ion), or reagents known to react with a given functional group (e.g., aryl nitroso plus glyoxylic acid aryl form hydroxamate plus $CO_2$). Preferably, however, protecting groups will be selected that do not cause significant interference with the binding reactions. Also, wash steps can be incorporated so that the byproducts do not interfere with the reactions.

Once localization of the anti-ligand is complete, the light pattern can be changed and the same or a different anti-ligand can be localized at other discrete sites on the surface. An anti-ligand, as noted above, is one or more molecules that recognize a particular ligand in solution. Examples of ligands that can be investigated by this invention include, but are not restricted to agonists and antagonists for cell membrane receptors, toxins and venoms, viral epitopes, antigenic determinants, hormones, hormone receptors, steroids, peptides, enzymes, substrates, cofactors, drugs, lectins, sugars, oligonucleotides, oligosaccharides, proteins, and monoclonal and polyclonal antibodies.

Anti-ligands that are nucleic acids are especially preferred. Suitable anti-ligands include relatively small, single molecules, such as cofactors, which show specific binding properties. Typically, anti-ligands will be greater than about 100 daltons in size and more typically will be greater than about 1 kD in size. Other examples of anti-ligands include, but are not restricted to, the common class of receptors associated with the surface membrane of cells and include, for instance, the immunologically important receptors of B-cells, T-cells, macrophages, and the like. Other examples of anti-ligands that can be investigated by this invention include, but are not restricted to, hormone receptors, hormones, drugs, cellular receptors, membrane transport proteins, steroids, peptides, enzymes, substrates, cofactors, vitamins, lectins, sugars, oligonucleotides, oligosaccharides, viral epitopes, antigenic determinants, glycoproteins, and immunoglobulins, e.g., monoclonal and polyclonal antibodies.

In a preferred embodiment, a plurality of anti-ligands are immobilized on a surface by first attaching photoreactive caged thiols to the surface. The caged thiols on a predefined region of the surface are exposed to light to give reactive thiol groups. The reactive thiol groups on the predefined region are then incubated with the anti-ligand to be immobilized, the surface is washed free of unreacted anti-ligand, and the surface is incubated with a desired ligand. The exact incubation conditions, e.g., time, temperature, pH, etc., will depend upon the species used and will be readily apparent to one skilled in the art. After washing the surface free of unbound anti-ligand, the above steps can be repeated on a different region of the surface with a different anti-ligand. In this fashion, a small, dense array of, e.g., oligonucleotide probes, can be prepared.

A surface prepared according to the methods described above can be used to screen for ligands having high affinity for immobilized anti-ligands. Screening can be performed by immobilizing a plurality of anti-ligands on predefined regions of a surface by the methods described above. A solution containing a marked (labelled) ligand is introduced to the surface and incubated for a suitable period of time. The surface is then washed free of unbound ligand, and the anti-ligands having high affinity for the ligand are identified by identifying those regions on the surface where markers are located. Suitable markers include, but are not limited to, radiolabels, chromophores, fluorophores, chemiluminescent moieties, and transition metals. When autoradiography is the detection method used, the marker is a radioactive label, such as $^{32}P$. The marker on the surface is exposed to X-ray film, which is developed and read out on a scanner. An exposure time of about 1 to 24 hours is typical. Fluorescence detection using a fluorophore label, such as fluorescein, attached to the ligand will usually require shorter exposure times. Alternatively, the presence of ligands may be detected using a variety of other techniques, such as an assay with a labelled enzyme, antibody, or the like. Other techniques using various marker systems for detecting bound ligand will be readily apparent to those skilled in the art.

In a preferred embodiment, a substrate prepared as discussed above can be exposed to a solution containing one or more ligands such as nucleic acids. The ligand can be labeled in any of a variety of ways, but in one embodiment, labeling of the ligand is effected with an oligonucleotide probe having a radioactive (or other)

label and complementary to the ligand nucleic acid. The ligand nucleic acid binds with high affinity to an immobilized nucleic acid previously localized on the surface and to the complementary labeled probe. After washing the surface free of nonspecifically bound ligand and labeled probe, the surface is placed proximate to X-ray film, if a radioactive label is employed, to identify the nucleic acids on the surface complementary to the nucleic acid ligand. Alternatively, a fluorescent label can be used, and detection can be accomplished with a charge-coupled device (CCD), fluorescence microscopy, or laser scanning.

In another embodiment useful for performing many parallel hybridization reactions in solution in a single reaction vessel using an immobilized array of probes, one uses a set of capture probes in solution. The capture probes are designed to have a sequence complementary to the target sequence to be detected and a sequence complementary to an immobilized probe located at one or more discrete locations on the surface of the substrate. In this system, either the capture probe is labeled or another labeled probe complementary to the target sequence to be detected is employed. This system allows the hybridization of probe to target sequence to be carried out in solution, because the immobilized probe array does not have to be (but can be, if desired) present in the reaction mixture during hybridization of the capture probe to the target sequence. This system also allows one to design the capture sequence, the complementary sequence of nucleotides in the immobilized probe and the capture probe, without constraint from the target sequence. These advantages allow one to perform an assay for many different target nucleic acids simultaneously and yet still identify whether any particular target nucleic acid is present in the sample tested.

Quantitative assays for ligand concentrations can also be performed according to the present invention. In a direct assay method, the surface containing localized anti-ligands prepared as described above is incubated with a solution containing a labeled ligand for a suitable period of time. The surface is then washed free of unbound ligand. The amount of label present at predefined regions of the surface is then measured and can be related to the amount of ligand in solution. Methods and conditions for performing such assays are well-known and are presented in, for example, Hood et al, *Immunology* (Benjamin/Cummings 1978) and Harlow et al, *Antibodies: A Laboratory Manual* (Cold Spring Harbor Laboratory 1988), each of which is incorporated herein by reference. See also U.S. Pat. No. 4,376,110, incorporated herein by reference, for methods of performing sandwich assays. The precise conditions for performing these steps will be apparent to one skilled in the art.

A competitive assay method can also be employed using the methods and reagents of the present invention. Such a method involves immobilizing anti-ligands on predefined regions of a surface as described above. An unmarked ligand is then bound to anti-ligands on the surface having specific binding affinity for the ligand. A solution containing marked ligand is then introduced to the surface and incubated for a suitable time. The surface is then washed free of unbound reagents, and the amount of marker remaining on the surface is measured. Alternatively, marked and unmarked ligand can be exposed to the surface simultaneously. The amount of marker remaining on predefined regions of the surface can be related to the amount of unknown ligand in solution.

The invention is illustrated in the Examples below primarily with reference to the identification of specific nucleic acid sequences in a sample. The invention will, however, find many other uses. For example, the invention can be used in information storage (e.g., on optical disks), production of molecular electronic devices, production of stationary phases in separation sciences, and in immobilization of cells, proteins, lectins, nucleic acids, polysaccharides and the like in any desired pattern on a surface via molecular recognition of a specific anti-ligand linked via a thiol group to a surface of a substrate.

The above description is intended to be illustrative and not restrictive. Many embodiments will be apparent to those of skill in the art upon reviewing the above description. The scope of the invention should, therefore, be determined not with reference to the above description or the following Examples, but should instead be determined with reference to the appended claims, along with the full scope of equivalents to which such claims are entitled.

EXAMPLE 1

Preparation of Substrate and Thiol-derivatized Surface

A. Preparation of Substrate Surface

Commercially available glass microscope slides (for example, 1"×3" smooth cut, 0.7 mm thick, anti-scratch coated slides or 2"×3" smooth cut, 0.7 mm thick, anti-scratch coated slides from Erie Scientific) were derivatized with t-BOC-aminopropyltriethoxy silane in substantial accordance with the procedure described in *J. Chromatography* 97:33 (1974), incorporated herein by reference.

Thus, the slides were cleaned by soaking in 10% Micro detergent (Baxter), individually scrubbed, and immersed in deionized water. The slides were then subjected to a 10 minute sonication in a 70° C. solution of 10% Micro detergent and rinsed ten times with deionized water. This process was followed by a three minute immersion in a 70° C. solution of 10% (w/v) NaOH. The slides were then rinsed ten times with deionized water, and then immersed for one minute in 1% HCl. The slides were then again rinsed ten times with deionized water, and then subjected to another 10 minute sonication in 70° C. deionized water, after which the slides were rinsed three to four times in deionized water. The slides were then ethanol rinsed and dried with nitrogen or argon. The slides were then inspected visually for spots and scratches in a yellow light with a black background, and any slides that were scratched or spotted or that still retained the anti-scratch coating were either discarded or recleaned.

An alternate or additional cleaning procedure is carried out as follows. The slides are loaded into teflon racks and subjected to a thirty minute immersion in a solution composed of Nochromix (Aldrich) with 36 g/L of concentrated sulfuric acid (which can be regenerated if discolored) that has been filtered (glass fiber filter) to remove particulate matter. Occasional agitation is provided during the thirty minute immersion step. The slides are then rinsed for one minute in deionized water with vigorous agitation. The slides are then placed for ten minutes in a rinse tank with 14 psi argon or nitrogen bubbling, a full open deionized water tap, and occasional agitation.

The slides are then immersed for three minutes in a 70° C. solution of 10% (w/v) NaOH, followed by a one minute rinse with deionized water and vigorous agitation, followed by a ten minute rinse in a rinse tank. The slides are then immersed for one minute in 1% HCl and then rinsed for five minutes in a rinse tank. The slides are then ethanol rinsed, dried with nitrogen or argon, and inspected visually for spots and scratches.

The t-BOC aminopropyl derivatization is carried out as follows. The slides are loaded into plastic staining jars, with about nine slides per jar. Preferably, the slides are completely dry when placed in the staining jars, and the silation reagents are added as follows. The silation reagent is a premixed solution of a 1:10 molar ratio of t-BOC-aminopropyltriethoxysilane:methyltriethoxysilane (i.e., 1 mL of t-BOC-aminopropyltriethoxysilane and 5.86 mL of methyltriethoxysilane, which is kept anhydrous and stored under argon). The silation reagent is diluted to 1% (v/v) in dichloromethane (DCM), mixed well, and 60 mL of the diluted silation reagent are added to each jar. The jars are capped and incubated overnight at room temperature. Then, the slides are removed from the jar, rinsed first with DCM and then with toluene and then dried immediately with argon. The slides are then loaded onto glass drying racks, inspected for streaks, and allowed to stand for approximately thirty minutes. The slides are then baked for one hour in a 100° C. oven with the glass racks in metal trays covered with foil. The oven should be no hotter than 110° C. The slides are then cooled and optionally numbered with an engraving tool.

The slides, prepared as described above, were then incubated at room temperature in a solution of 50% trifluoroacetic acid/50% DCM for forty minutes to remove the t-BOC protecting group. After being washed sequentially with DCM and then twice with a solution of 5% diisopropylethylamine (DIEA) in methylene chloride for 5 minutes each wash, the slides were then washed with methylene chloride, then with ethanol, and then the slides were dried with argon. The slides were derivatized within one hour of drying.

B. Preparation of Nitroveratrylthiolpropionic Acid

Nitroveratrylthiolpropionic acid was prepared in substantial accordance with the protocols set forth in Patchornik et al, 21 Oct. 1970, *J. Am. Chem. Soc.* 92(21):6333–6335, incorporated herein by reference.

About 500 mg (0.0018 moles) of bromonitroveratryl (NVBr) were added to a solution containing 160 μL (0.0018 moles) of thiolpropionic acid ($HSCH_2CH_2CO_2H$), 6 mL of dimethylformamide (DMF), and 364 mg (0.0036 moles) of triethylamine ($Et_3N$). After about five minutes, a precipitate ($Et_3N^+HBr$) formed, and the reaction was-deemed complete after analysis with thin layer chromatography (TLC in 10% methanol/dichloromethane). The reaction mixture was then diluted with 100 mL of methylene chloride and washed with 50 mL of 1N NaOH. The aqueous phase was separated, acidified with 1N HCl, extracted with methylene chloride, and then the organic layer was dried ($Na_2SO_4$), and then rotary evaporated to dryness. About 0.54 g of nitroveratrylthiolpropionic acid was obtained. The product can be further purified by dissolving the product in ethanol, adding five volumes of water, and collecting the needle-shaped crystals by filtration.

C. Coupling of Nitroveratrylthiolpropionic Acid to Substrate Surface

A solution composed of 60 mg of nitroveratrylthiolpropionic acid, 70 μL of DIEA, 29.8 mg of HOBT (1-hydroxybenzotriazole hydrate), and 0.2 mL of DMF was mixed at room temperature for 10 minutes with a solution composed of 88.5 mg of BOP (benzotriazol-1-yloxytris-(dimethylamino) phosphonium hexafluorophosphate) and 0.2 mL of DMF. The resulting mixture was then diluted with 1.6 mL of DMF, and about 0.5 mL of the resulting mixture was applied to each 1"×3"slide. The slides were then immersed with a 3:1 (v/v) solution of pyridine:acetic anhydride with 0.1% DMAP (4-dimethylaminopyridine). The resulting slides were then used in the coupling and hybridization experiments described below.

EXAMPLE 2

Coupling of Fluorescein Maleimide to Substrate Surface

A glass microscope slide prepared as described in Example 1C was mounted on a custom flow cell and illuminated through a 500 μm×500 μm checkerboard-pattern mask (Photo Sciences Inc., Torrance, Calif.) using broad-band UV/blue light. This pattern was repeated in triplicate on each slide, and the illumination was carried out so that one region underwent a four minute photolysis, a second region underwent a two minute hydrolysis, and a third region underwent a one minute photolysis. The light source was a 500 W Mercury arc lamp (Oriel Model 87330) equipped with a 350 nm–450 nm dichroic reflector that produced actinic light having an intensity of 12 mW/cm$^2$ as measured through a 360 nm bandpass filter. The derivatized surface was photolyzed in flowing dioxane for 15 minutes and then rinsed in ethanol and dried with argon.

About 4.3 mg of fluorescein maleimide (Molecular Probe) were dissolved in 10 mL of warm DMF to obtain a one mM solution of fluorescein maleimide. This solution was allowed to cool to room temperature, and then the slide was immersed in the solution and incubated at room temperature for two hours with gentle agitation. The slide was then removed from the solution and rinsed sequentially with DMF, ethanol, methylene chloride, and again with ethanol, and then the slide was dried with argon.

The slide was examined with a scanning fluorescence microscope (Zeiss Axioskop equipped with a Newport Model PM500C-motion controller, a Spectra-Physics Model 2020 argon-ion laser producing a 488 nm excitation light; and a 520 nm long-pass emission filter) interfaced with a photon-counting device (Hamamatsu Model 9403-02 photomultiplier; Stanford Research Systems Model SR445 amplifier and Model SR430 multichannel scaler, IBM compatible PC) to generate a two-dimensional image consisting of fluorescence intensity data as a function of x,y position. The results of this analysis revealed the pattern of illuminated and dark squares expected from the fluorescein maleimide coupling to the deprotected thiol groups in the illuminated squares. This experiment demonstrates that the photochemically protected thiols are competent for coupling to a maleimide-containing compound after photodeprotection.

EXAMPLE 3

Coupling of Oligonucleotides with Thiol-reactive Groups to Substrate Surface

This example shows the results of a test for the effectiveness of several different thiol-reactive groups that, when attached to an oligonucleotide, enable covalent coupling to thiol-derivatized glass slides.

A 5'-fluoresceinated 3'-C6-amino oligonucleotide probe (designated CAP2, which was prepared using the Clonetech reagent 3'-C6-amino-modifier-CPG) was activated with the following heterobifunctional reagents: (1) succinimidyl bromoacetate (BrAc-NHS); (2) succinimidyl iodoacetate (IAc-NHS); (3) succinimidyl 6-((iodoacetyl)amino)hexanoate (SIAX); (4) succinimidyl 6- ( 6-(((iodoacetyl)amino)hexanoyl)amino)hexanoate (SIAXX); and (5) succinimidyl 6-maleimidylhexanoate (EMCS). The activation reactions were carried out in separate reaction mixtures containing: 0.2 mM oligonucleotide; 0.25 M Na borate, pH=8.3; 40 mM of one of the five NHS esters listed above; 24% acetonitrile; and 24% DMF, typically in a total volume of 200 μL. The reaction was incubated at 25° C. for 30 minutes, and the resulting modified oligonucleotide was desalted on a G-25 spin column (unbuffered water) and then used without further purification at a concentration of about 100 μM (determined spectrophotometrically). Polyacrylamide gel electrophoresis assays after quenching with a fluorescent thiol indicated that about 75% of the oligonucleotides were modified in the reaction.

The modified oligonucleotides were applied at a concentration of about 100 μM in unbuffered water to a freshly photolyzed thiol-containing slide prepared as described in Example 1. About 5 μL of each oligonucleotide were applied to each well on the slide. The wells were created on the slide using a twelve well template with O-rings to seal the template to the slide. After each oligonucleotide was added to a well, about 5 μL of a buffer solution composed of 100 mM HEPES, pH=8.0, 5 mM EDTA, and 5 mM DTAB (dodecyl trimethyl ammonium bromide) were added to each well to initiate the reaction. The reaction mixtures were incubated at room temperature for four hours in the dark, and then the wells were rinsed with water and the slide was removed and washed in a solution composed of 2% SDS in Tris-buffer at pH=8 at 65° C. overnight. The slides were then washed with water and ethanol, then dried. Surface fluorescence on the slide was then imaged using a scanning 488 nm laser induced fluorescence microscope. Average fluorescence intensities per pixel in the immobilization sites were used as a measure of oligonucleotide binding.

Figure 1:
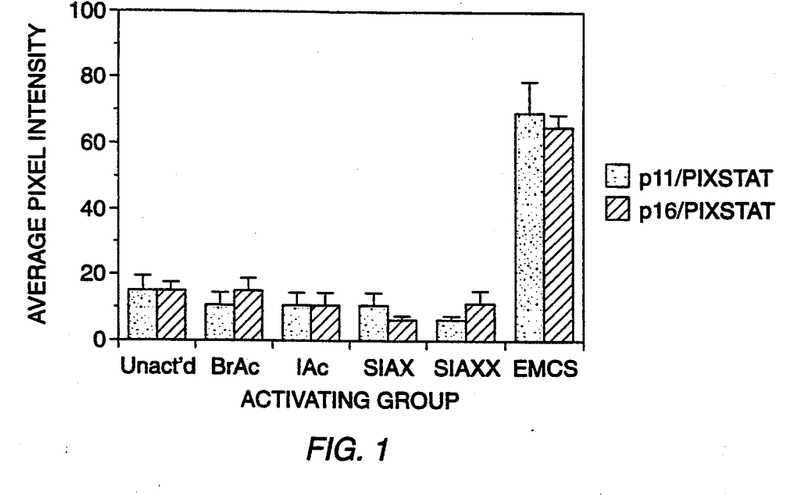
FIG. 1 presents the results of fluorescence excitation scanning of a slide on which a variety of activated oligonucleotides have been immobilized through covalent linkage to thiol groups on the slide; the results show that oligonucleotides activated with succinimidyl 6-maleimidylhexanoate are preferred for coupling to the thiol group-containing solid supports of the present invention (see Example 3).

The results of the scanning are presented graphically in FIG. 1. The results show that none of the haloacetyl activating groups enhanced binding significantly above the background non-specific binding but that the maleimide activating group (EMCS) enhanced binding fivefold over background non-specific binding. These results do not indicate that the other activating groups tested (including cyanuric chloride, tested in a separate experiment) are unsuitable for coupling to the substrates of the invention but instead indicate that of the activating groups tested, the maleimide activating group is preferred under the conditions employed.

EXAMPLE 4

Coupling Efficiency of Maleimide-activated Oligonucleotides to Substrate Surface—Effect of Various Additives This example shows the results of the addition of a variety of additives on the coupling efficiency of a maleimide-activated, 5'-fluoresceinated oligonucleotide to thiol-derivatized slides. In this example, the 5'-fluoresceinated 3'-C6-amino oligonucleotide was activated with succinimidyl 6-maleimidylhexanoate and applied to a freshly photolyzed slide as a solution in water in substantial accordance with the procedure set forth in Example 3.

Figure 2:
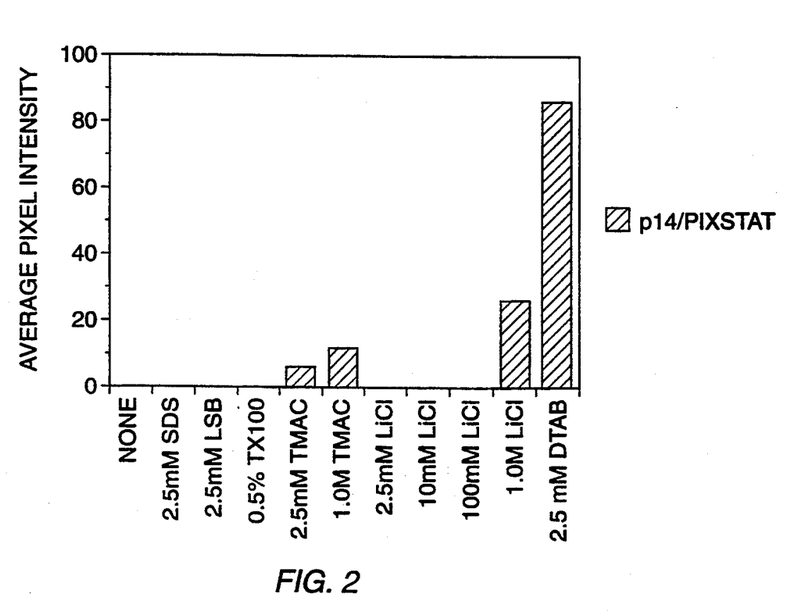
FIG. 2 presents the results of fluorescence excitation scanning of a slide on which oligonucleotides have been immobilized through covalent linkage to thiol groups on the slide in the presence of different additives; the results show that the anionic, zwitterionic, and neutral detergents do not appear to enhance coupling efficiency; the salts TMAC (trimethylammonium chloride) and LiCl give a moderate enhancement in coupling efficiency; and the cationic detergent DTAB causes a large enhancement in coupling efficiency at relatively low concentrations (see Example 4).

Each different additive was added to the coupling initiation buffer (100 mM HEPES, pH=8..0, 5 mM EDTA, and the additive). After the coupling reaction, the slides were washed and scanned as described in Example 3. The results of the scanning are presented graphically in FIG. 2. The results show that the anionic, zwitterionic, and neutral detergents did not appear to enhance coupling efficiency; the salts TMAC (trimethylammonium chloride) and LiCl gave a moderate enhancement in coupling efficiency; and the cationic detergent DTAB caused a large enhancement in coupling efficiency at relatively low concentrations (2.5 mM; at higher concentrations, greater than 10 mM, the oligonucleotide precipitated). Other additives of interest include compounds such as spermidine, spermine, polyamines, polyethyleneimine, and other cationic detergents similar to DTAB, and other salts similar to LiCl.

EXAMPLE 5

Hybridization of Nucleic Acids to Immobilized Oligonucleotide

Two glass slides prepared in accordance with the procedures set forth in Examples 3 and 4 were tested for ability to hybridize specifically with a complementary oligonucleotide. The two slides differed with respect to the additive present during the coupling reaction; one slide was coupled to oligonucleotide in the presence of LiCl, the other in the presence of DTAB.

The slides were prehybridized individually in heat sealed bags at 56° C. with a solution composed of 6X SSC, 6X Denhardt's solution, 0.5% SDS, and 100 μg/mL of sheared, denatured, salmon sperm DNA. The hybridization reaction was carried out at 53.5° C. ($T_M$ minus 5° C.) in prehybridization buffer containing 1 pmole of a s$^{32}$P-end labeled 60mer probe (specific activity of $1.5 \times 10^8$ CPM/μg) containing a 30 nucleotide segment perfectly complementary to the covalently coupled oligonucleotide probe. The hybridized slides were evaluated in a beta plate counter and by autoradiography.

The results showed that the labeled probe hybridized specifically to the covalently coupled oligonucleotide with very little background.

EXAMPLE 6

Rehybridization of Nucleic Acids to Oligonucleotide-derivatized Substrate Surface The slides hybridized to labeled probe in accordance with the procedure of Example 5 were washed three times with a 100° C solution of 0.01% SDS. The slides were then allowed to expose XAR film overnight at −70° C. to determine whether the labeled probe had been removed. The results showed complete removal of the probe from all but two sites, which showed only weak signal.

Rehybridization with the labeled probe of Example 5 was carried out using the Stratagene Qwik-Hyb ™ hybridization accelerator solution following the package insert directions. Other hybridization acceleration reagents that can be employed in the methods of the present invention include A1 protein, RecA protein, SSB, dextran sulfate, ficoll, phenol, and detergent. Prehybridization was carried out for 15 minutes at 53.5° C., and then 100 μL of 10 mg/mL salmon sperm DNA was added to the slides together with 10 μL (one pmole) of the labeled probe. The hybridization reaction was carried out at 53.5° C. for one hour. The slides were washed and then allowed to expose XAR film overnight at −70° C.

The results showed that the slides to which oligonucleotide had been coupled in LiCl gave an even stronger signal than after the first hybridization and that the slides to which oligonucleotide had been coupled in DTAB gave a weaker but still clear signal than after the first hybridization. Both slides showed very little background signal.

then washed for 12 hours in a 65° C. solution of 2% SDS.

The slide is then hybridized to a first labeled target nucleic acid complementary to probe CAP2, and the specificity of hybridization is determined. The slide is then washed to remove the labeled target nucleic acid, and a second labeled target nucleic acid complementary to probe CAP5 is added, and the specificity of hybridization is determined. The results demonstrate that the methods and reagents of the invention provide a very sensitive and specific assay for target nucleic acid sequences.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

CCAACTCTTT TTCCGAAGGT AACTGGCTTC                    30

( 2 ) INFORMATION FOR SEQ ID NO:2:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

GTTCCGCAGG TTCTCTCGGT CAGTCTGTGC                    30

EXAMPLE 7

Specific Hybridization of Nucleic Acids to Immobilized Oligonucleotide Probe Array A slide prepared as described in Example 1 is photolyzed under dioxane and then rinsed with ethanol and dried under a nitrogen stream. The slide is clamped to a template that forms a well over the photolyzed area, and 20 μL of a 100 μM solution of 3'-EMCS-activated probe CAP2 (5'-CCAACTCTTTTTCCGAAGG-TAACTGGCTTC [SEQ. ID NO. 1]) in unbuffered water and HEPES/EDTA/DTAB buffer are added to the well. The slide and template are then incubated at room temperature for two hours, the reaction is quenched by the addition of N-ethyl maleimide, and the slide is rinsed liberally first with water and then with dioxane. The slide is then re-photolyzed to activate a different region on the slide and then coupled to 3'-ECMS-activated probe CAP5 (5'-GTTCCGCAGGTTCTCTCGGTCAGTCTGTGC [SEQ. ID NO.2]). After the coupling reaction is quenched as before, the slide is rinsed with water and

What is claimed is:

1. A method for forming predefined regions on a surface of a solid support, the method comprising the steps of:
   a) covalently coupling thiolpropionate having a photochemically removable protecting group, the protecting group selected from the group consisting of nitroveratryl, 1-pyrenylmethyl, 6-nitroveratryloxycarbonyl, dimethyldimethoxybenzyloxycarbonyl, nitrobenzyloxycarbonyl, 5-bromo-7-nitroindolinyl, O-hydroxy-alpha-methyl-cinnamoyl, methyl, 6-nitroveratryloxycarbonyl, methyl-6-nitropiperonyloxycarbonyl, and 2-oxymethylene anthraquinone, to functional groups on a surface of a solid support; and
   b) illuminating the surface with a light source of a wavelength of between 280 and 420 nm shone through a mask, thereby selectively irradiating the predefined regions of the surface to remove said photochemically removable protecting group from the thiolpropionate in the predefined regions.

2. The method of claim 1, wherein the solid support is a functionalized glass slide and the photochemically removable protecting group is nitroveratryl.

3. The method of claim 2, wherein said functionalized glass slide has been functionalized by treatment with t-BOC-aminopropyltriethoxysilane.

4. The method of claim 2, wherein the method further comprises covalently coupling and activated oligonucleotide to the deprotected thiolpropionate in said predefined regions.

5. The method of claim 4, wherein said activated oligonucleotide has been activated with succinimidyl 6-maleimidylhexanoate.

6. The method of claim 3, wherein the coupling step is carried out in the presence of a cationic detergent.

7. The method of claim 6, wherein the cationic detergent is dodecyl trimethyl ammonium bromide (DTAB).

* * * * *